US009683971B2

(12) United States Patent
Taki et al.

(10) Patent No.: US 9,683,971 B2
(45) Date of Patent: Jun. 20, 2017

(54) OBJECT INFORMATION ACQUIRING APPARATUS AND CONTROL METHOD THEREOF

(71) Applicant: CANON KABUSHIKI KAISHA, Tokyo (JP)

(72) Inventors: Hirofumi Taki, Kyoto (JP); Kenichi Nagae, Yokohama (JP); Toru Sato, Kyoto (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 440 days.

(21) Appl. No.: 14/251,723

(22) Filed: Apr. 14, 2014

(65) Prior Publication Data
US 2014/0318253 A1 Oct. 30, 2014

(30) Foreign Application Priority Data
Apr. 25, 2013 (JP) ................... 2013-092668

(51) Int. Cl.
*G01N 29/24* (2006.01)
*B06B 1/06* (2006.01)
(Continued)

(52) U.S. Cl.
CPC ........... *G01N 29/24* (2013.01); *B06B 1/0292* (2013.01); *B06B 1/0629* (2013.01);
(Continued)

(58) Field of Classification Search
CPC .............. G01N 29/24; G01N 2291/044; B06B 1/0292; B06B 1/0629; G01S 7/52047; G01S 15/8977; G10K 11/348
See application file for complete search history.

(56) References Cited

U.S. PATENT DOCUMENTS 2,837,728 A  6/1958 Schuck ............................ 340/9
4,425,525 A  1/1984 Smith et al. ................. 310/336
(Continued)

FOREIGN PATENT DOCUMENTS

CN  102015127  4/2011
CN  101883309  11/2011
(Continued)

OTHER PUBLICATIONS

Translation of Taki et al., JP Pat. App. 200929005 A.*
(Continued)

*Primary Examiner* — Lisa Caputo
*Assistant Examiner* — Nathaniel T Woodward
(74) *Attorney, Agent, or Firm* — Fitzpatrick, Cella, Harper & Scinto

(57) ABSTRACT

Adopted is an object information acquiring apparatus that includes: a probe including multiple conversion elements that transmit acoustic waves to an object, and convert the reflected waves into time-series received signals; and a processor that performs frequency domain interferometry, through application of adaptive signal processing, by using the multiple received signals output from the multiple conversion elements and a reference signal, and obtains acoustic properties of multiple positions. The probe is configured such that, when a direction in which the multiple conversion elements are arranged is a first direction and a second direction, end portions in the second direction have a lower transmission sound pressure of the acoustic waves than a midportion in the second direction.

14 Claims, 15 Drawing Sheets

(51) Int. Cl.
*B06B 1/02* (2006.01)
*G10K 11/34* (2006.01)
*G01S 7/52* (2006.01)
*G01S 15/89* (2006.01)

(52) U.S. Cl.
CPC ........ *G01S 7/52047* (2013.01); *G10K 11/348* (2013.01); *G01N 2291/044* (2013.01); *G01S 15/8977* (2013.01)

(56) References Cited

U.S. PATENT DOCUMENTS

| | | | |
|---|---|---|---|
| 4,460,841 A | 7/1984 | Smith et al. | 310/334 |
| 5,488,956 A | 2/1996 | Bartelt et al. | 128/662.03 |
| 6,359,367 B1 | 3/2002 | Sumanaweera et al. | 310/309 |
| 6,381,197 B1 | 4/2002 | Savord et al. | 367/178 |
| 7,212,466 B2 * | 5/2007 | Wilson | G01S 7/53 367/68 |
| 8,344,587 B2 | 1/2013 | Soeda | 310/309 |
| 8,784,317 B2 | 7/2014 | Taki et al. | 600/442 |
| 2005/0075572 A1 * | 4/2005 | Mills | B06B 1/0292 600/459 |
| 2007/0059858 A1 | 3/2007 | Caronti et al. | 438/50 |
| 2007/0193354 A1 | 8/2007 | Felix et al. | 73/514.32 |
| 2008/0259725 A1 | 10/2008 | Bayram et al. | 367/7 |
| 2010/0327380 A1 | 12/2010 | Chang | 257/419 |
| 2011/0208059 A1 | 8/2011 | Cerofolini | 600/447 |
| 2011/0307181 A1 | 12/2011 | Nagae | 702/19 |
| 2012/0259218 A1 | 10/2012 | Nagae et al. | 600/437 |
| 2012/0314534 A1 | 12/2012 | Yoda et al. | 367/7 |
| 2013/0338944 A1 | 12/2013 | Nagae et al. | 702/56 |
| 2014/0010052 A1 | 1/2014 | Torashima et al. | 367/181 |
| 2014/0051970 A1 | 2/2014 | Ebisawa et al. | 600/407 |
| 2014/0056105 A1 | 2/2014 | Nagae et al. | 367/87 |
| 2015/0091477 A1 | 4/2015 | Kandori et al. | 318/116 |

FOREIGN PATENT DOCUMENTS

| | | |
|---|---|---|
| CN | 102458692 | 5/2012 |
| EP | 0401027 | 12/1990 |
| EP | 2793048 A | 10/2014 |
| GB | 2114857 A | 8/1983 |
| JP | S58-161492 | 9/1983 |
| JP | H01-024479 | 5/1989 |
| JP | H01-024480 | 5/1989 |
| JP | H06-125894 | 5/1994 |
| JP | 2004-350703 | 12/2004 |
| JP | 2010-183979 | 8/2010 |
| JP | 2012-217624 | 11/2012 |
| JP | 2012-234208 | 11/2012 |
| WO | WO 2010/073534 | 7/2010 |
| WO | WO 2013/032021 A | 3/2013 |
| WO | WO 2013/088654 A | 6/2013 |

OTHER PUBLICATIONS

Translation of Taki et al. JPA 2010-183979.*
Extended European Search Report issued Jun. 2, 2015 in EPA 14163664.7 (in English).
Office Action issued on Jan. 13, 2016 in P.R. China patent application 201410171904.0, with translation.
Office Action issued on Dec. 23, 2015, in counterpart P.R. China patent application 201410180728.7, with translation.
H. Taki et al., "High Range Resolution Medical Acoustic Vascular Imaging with Frequency Domain Interferometry", *Proceedings of 32nd International Conference of the IEEE Engineering in Medicine and Biology Society*, pp. 5298-5301 ( 2010).
Extended European Search Report issued on Aug. 14, 2015 in counterpart EPA 14163665.4 (in English).
H. Taki et al., "High Resolution Medical Acoustic Vascular Imaging Using Frequency Domain Interferometry", *Ninth IASTED International Conference on Visualization, Imaging and Image Processing (VIIP 2009)*, pp. 7-12 (Jul. 13, 2009).
Extended European Search Report issued on May 12, 2015 in counterpart EPA 14163663.9 (in English).
Office Action issued Mar. 21, 2017 in counterpart Japanese patent application 2013-092668, with machine translation (6 pages).

* cited by examiner

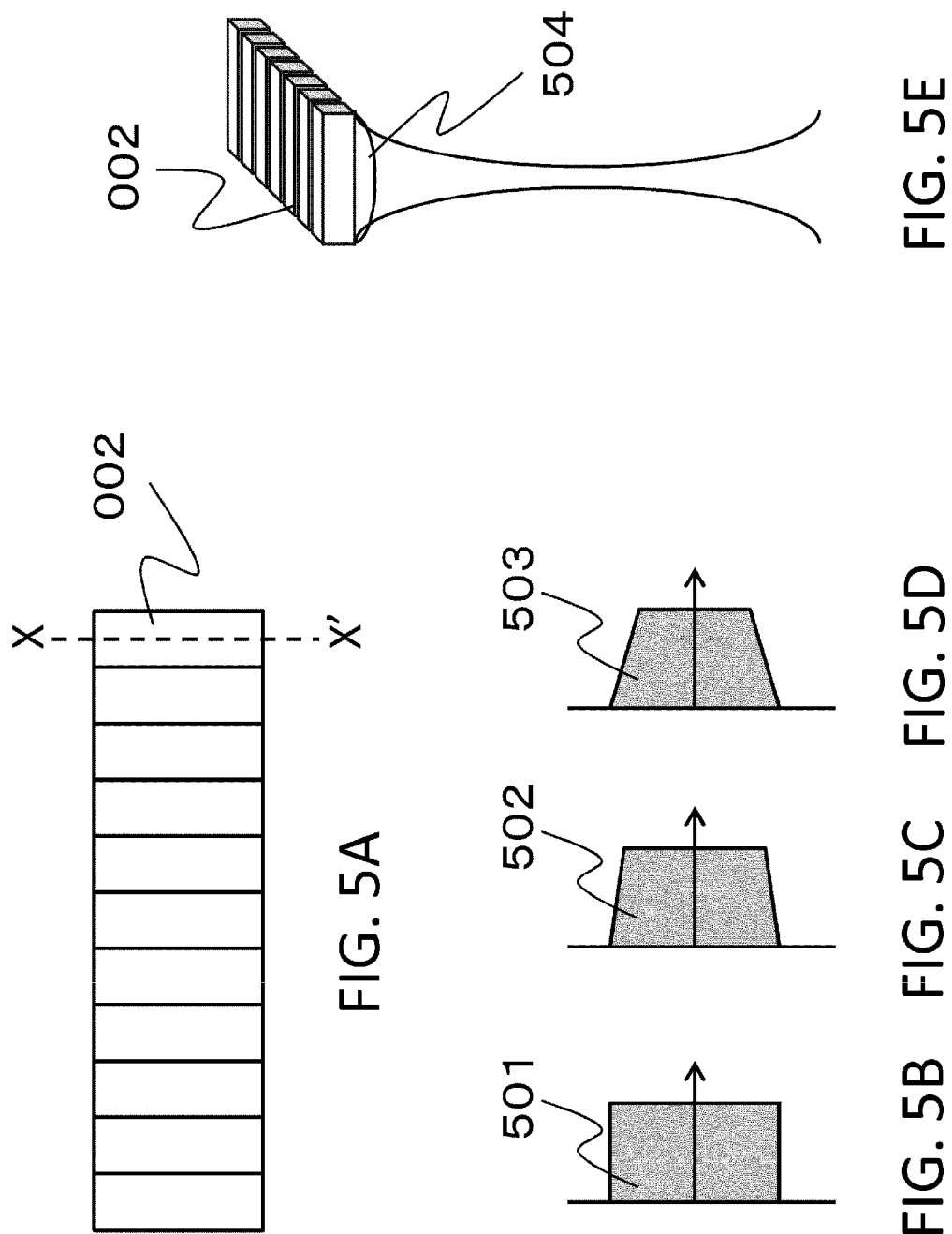

OBJECT INFORMATION ACQUIRING APPARATUS AND CONTROL METHOD THEREOF

BACKGROUND OF THE INVENTION

Field of the Invention

The present invention relates to an object information acquiring apparatus and a control method therefor. In particular, the present invention relates to technology for acquiring object information by transmitting acoustic waves to an object, and receiving reflected waves that are reflected within the object.

Description of the Related Art

In an ultrasonic diagnostic apparatus, which is an object information acquiring apparatus, the spatial resolution in the depth direction in the case of forming image data via the pulse-echo technique can be generally represented as $(n\lambda)/2$ when the wavelength of the ultrasonic waves is $\lambda$, and the transmission wave number is n. For instance, when two wavelengths worth of ultrasonic waves having a center frequency of 12 MHz are transmitted, the spatial resolution in the depth direction will be approximately 0.13 mm.

The pulse-echo technique is now explained. Foremost, when an ultrasonic pulse (acoustic wave pulse) is transmitted to an object, ultrasonic waves are reflected and returned according to the acoustic impedance difference within the object. Next, the reflected waves are received, and a received signal of the reflected waves is used to generate image data. Typically, an envelope of the received signal is acquired, and the acquired envelope is converted into a brightness value to generate image data. As a result of repeating the transmission and reception of ultrasonic waves to a plurality of directions or positions within the object, brightness information on a plurality of scanning lines in the direction that the ultrasonic waves were transmitted and received can be acquired. The inside of the object can be imaged by arranging the brightness information on the plurality of scanning lines.

Note that, in an ultrasonic diagnostic apparatus, a plurality of conversion elements are used for converting the ultrasonic waves into an electric signal, and, by adding a time shift to the received signal waveform between the respective elements, both transmission and reception are generally focused within the object.

As described above, while a spatial resolution in the depth direction of approximately 0.13 mm can be realized by using the pulse-echo technique, higher spatial resolution is being demanded. For example, if it is possible to observe the layer structure of the vascular wall of the carotid artery in further detail, this may contribute to the early detection of arteriosclerosis or the like.

Non Patent Literature 1 shows the results of imaging the layer structure of the vascular wall by performing frequency domain interferometry (the FDI method), and the Capon method, which is adaptive signal processing. As a result of performing the Capon method by using a received signal and applying the FDI method, it is possible to further improve the spatial resolution in the depth direction (scanning line direction). However, it is assumed that there are a plurality of reflecting layers within the signal range (processing range) in the depth direction that was cut out for performing FDI processing. Moreover, it is likely that the plurality of reflected waves from adjacent reflecting layers will mutually have high correlation. When adaptive signal processing such as the Capon method is directly applied to the received signal of a plurality of reflected waves having high correlation as described above, it is known that unexpected operations such as the negation of intended signals tend to occur. In order to reduce the influence from signals having the foregoing correlation (correlative interference waves), the FDI method and the Capon method can be applied to the received signal of the reflected waves by additionally using the frequency averaging technique.

In addition, upon adopting the frequency averaging technique for a received signal of acoustic waves having a broad frequency band such as with pulse waves, whitening of the received signal is performed using a reference signal. Patent Literature 1 describes an ultrasonic probe capable of suppressing the sidelobe level by causing the backing material to have distribution.

Patent Literature 1: Japanese Patent Application Laid-Open No. H6-125894

Patent Literature 2: Japanese Examined Patent Publication No. H1-24479

Patent Literature 3: Japanese Examined Patent Publication No. H1-24480

Non Patent Literature 1: Hirofumi Taki, Kousuke Taki, Takuya Sakamoto, Makoto Yamakawa, Tsuyoshi Shiina and Toru Sato: Conf Proc IEEE Eng Med Biol Soc. 2010; 1: 5298-5301.

As described above, a reference signal is used in the adaptive signal processing to which the FDI method is applied. The closer this reference signal is to the actually acquired reflected waveform, the greater the effect of achieving higher spatial resolution based on the adaptive signal processing to which the FDI method is applied.

Nevertheless, in effect, with the acoustic wave pulse that is transmitted into the object, the waveform will change depending on the position of its arrival (reflected position). In particular, at positions of different depths, the waveform of the transmitted acoustic wave pulse tends to differ. Thus, there were cases where the effect of achieving higher spatial resolution based on the adaptive signal processing to which the FDI method is applied could not be sufficiently yielded.

SUMMARY OF THE INVENTION

The present invention was devised in view of the foregoing problems, and an object of this invention is to inhibit the influence caused by the deterioration in the spatial resolution, depending on the position, upon performing the adaptive signal processing to which the FDI method is applied.

The present invention provides an object information acquiring apparatus, comprising:

a probe including a plurality of conversion elements configured to transmit acoustic waves to an object, receive reflected waves that were reflected within the object, and convert the reflected waves into time-series received signals; and a processor configured to perform frequency domain interferometry, through application of adaptive signal processing, by using a plurality of the received signals output from the plurality of conversion elements and a reference signal, and obtain acoustic properties of a plurality of positions in the object, wherein the probe is configured such that, when a direction in which the plurality of conversion elements are arranged is a first direction and a direction which intersects with the first direction is a second direction, end portions in the second direction have a lower transmission sound pressure of the acoustic waves than a midportion in the second direction.

The present invention also provides an object information acquiring apparatus, comprising:

a probe including a conversion element group for transmission having a plurality of conversion elements that transmit acoustic waves to an object, and a conversion element group for reception having a plurality of conversion elements that receive reflected waves reflected within the object, and convert the reflected waves into time-series received signals; and a processor configured to perform frequency domain interferometry, through application of adaptive signal processing, by using a plurality of the received signals output from the conversion element group for reception and a reference signal, and obtaining acoustic properties of a plurality of positions in the object, wherein the probe is configured such that, when a direction in which the plurality of conversion elements of the conversion element group are arranged is a first direction and a direction which intersects with the first direction is a second direction, end portions in the second direction have a lower transmission sound pressure of the acoustic waves than a midportion in the second direction in the conversion element group for transmission, or configured such that reception intensity of the acoustic waves is lower at the end portions in the second direction than at the midportion in the second direction in the conversion element group for reception.

The present invention also provides a control method of an object information acquiring apparatus having a probe including a plurality of conversion elements that transmit and receive acoustic waves, and a processor, with the probe being configured so that, when a direction in which the plurality of conversion elements are arranged is a first direction and a direction which intersects with the first direction is a second direction, end portions in the second direction have a lower transmission sound pressure of the acoustic waves than a midportion in the second direction, the control method comprising:

a step of operating the plurality of conversion elements to transmit acoustic waves to an object;

a step of operating the plurality of conversion elements to receive reflected waves reflected within the object, and convert the reflected waves into time-series received signals; and a step of operating the processor to perform frequency domain interferometry, through application of adaptive signal processing, by using a plurality of the received signals output from the plurality of conversion elements, and a reference signal, and obtain acoustic properties of a plurality of positions in the object.

The present invention also provides a control method of an object information acquiring apparatus having a probe including a conversion element group for transmission having a plurality of conversion elements that transmit acoustic waves and a conversion element group for reception having a plurality of conversion elements that receive reflected waves, and a processor, with the probe being configured such that, when a direction in which the plurality of conversion elements of the conversion element group are arranged is a first direction and a direction which intersects with the first direction is a second direction, end portions in the second direction have a lower transmission sound pressure of the acoustic waves than a midportion in the second direction in the conversion element group for transmission, or configured such that reception intensity of the acoustic waves is lower at the end portions in the second direction than at the midportion in the second direction in the conversion element group for reception, the control method comprising:

a step of operating the conversion element group for transmission to transmit acoustic waves to an object;

a step of operating the conversion element group for reception to receive reflected waves reflected within the object, and convert the reflected waves into time-series received signals; and a step of operating the processor to perform frequency domain interferometry, through application of adaptive signal processing, by using a plurality of the received signals output from the conversion element group for reception and a reference signal, and obtain acoustic properties of a plurality of positions in the object.

According to the present invention, it is possible to inhibit the influence caused by the deterioration in the spatial resolution, depending on the position, upon performing the adaptive signal processing to which the FDI method is applied.

Further features of the present invention will become apparent from the following description of exemplary embodiments with reference to the attached drawings.

BRIEF DESCRIPTION OF THE DRAWINGS

FIG. 5A to FIG. 5E are diagrams explaining the conversion elements and the transmission sound pressure distribution thereof;

DESCRIPTION OF THE EMBODIMENTS

The preferred embodiments of the present invention are now explained with reference to the appended drawings. However, the size, material, shape and relative arrangement of components described below are to be suitably changed depending on the configuration and various conditions of the apparatus to which the present invention is to be applied, and these embodiments are not intended to limit the scope of the present invention to the following descriptions.

The present inventors focused attention on the fact that the waveform of the transmitted acoustic waves varies depending on the position within the object upon performing adaptive signal processing to which the FDI method is applied by receiving reflected waves from that object. Subsequently, the present inventors discovered that there is a possibility that the image will deteriorate if there is variance in waveforms between the reflected waveform and the waveform of the reference signal caused by the variance in the transmission waveform.

Figure 1:
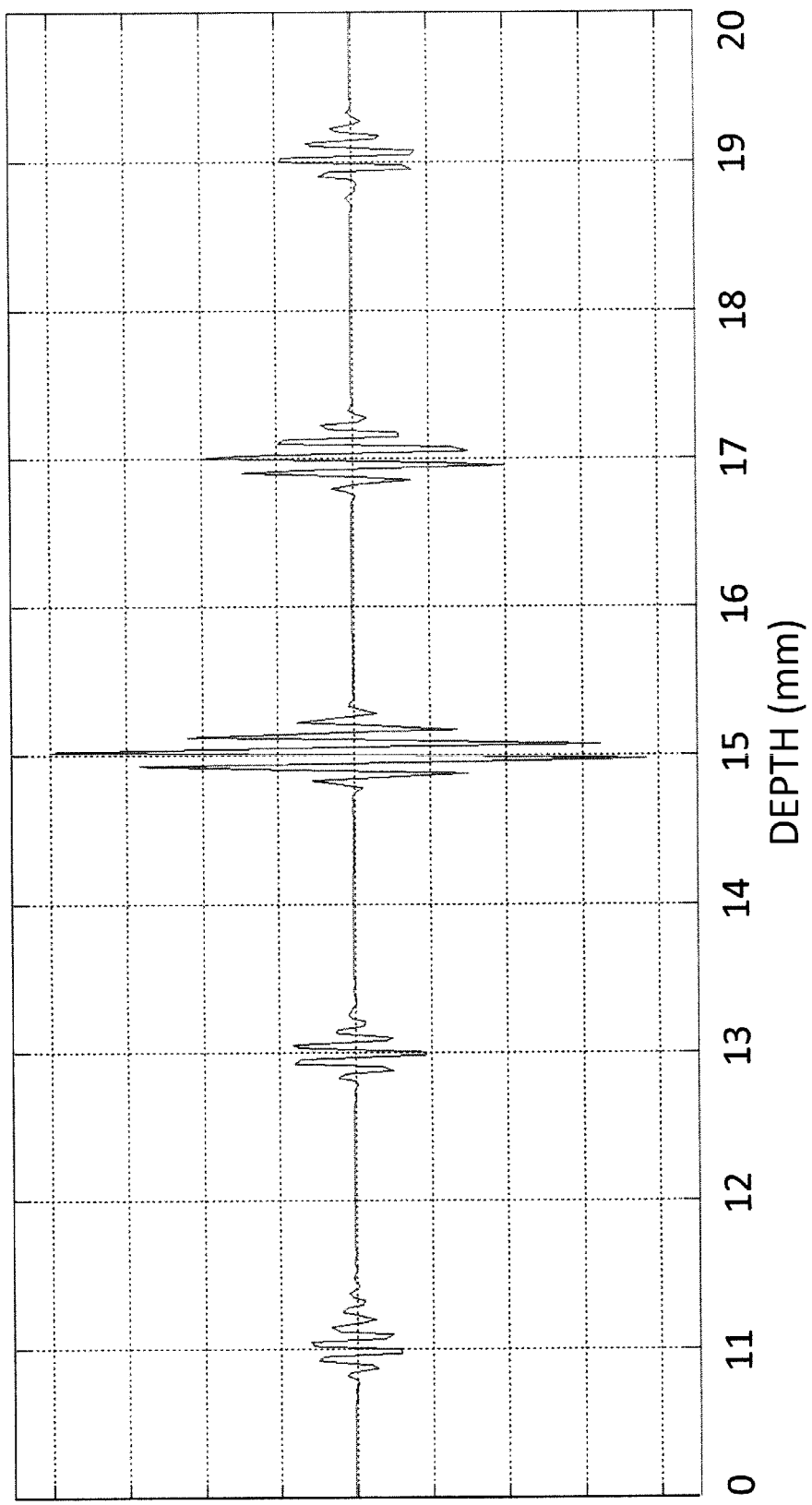
FIG. 1 is a diagram explaining the reflected waveform.

For instance, explained is a case of transmitting acoustic waves from a probe in which conversion elements are arranged in a line in a one-dimensional direction. FIG. 1 shows the waveforms of the acoustic wave pulse, at the respective depths of 11 mm, 13 mm, 15 mm, 17 mm, and 19 mm, that are transmitted from a linear array in which a plurality of conversion elements are arranged one-dimensionally and focused at a depth of 15 mm. The term "depth" as used herein refers to the distance from the conversion elements. In this example, since the transmission focus is at 15 mm, the waveform at the depth of 15 mm will basically be the same as the transmission waveform. Nevertheless, as evident from FIG. 1, the waveform differs from the transmission waveform (that is, the waveform at 15 mm) at the other depths (11 mm, 13 mm, 17 mm, 19 mm). In particular, it can be seen that the waveform at a shallow position (position in which the distance is short from the conversion elements) considerably differs from the transmission waveform.

Figure 2:
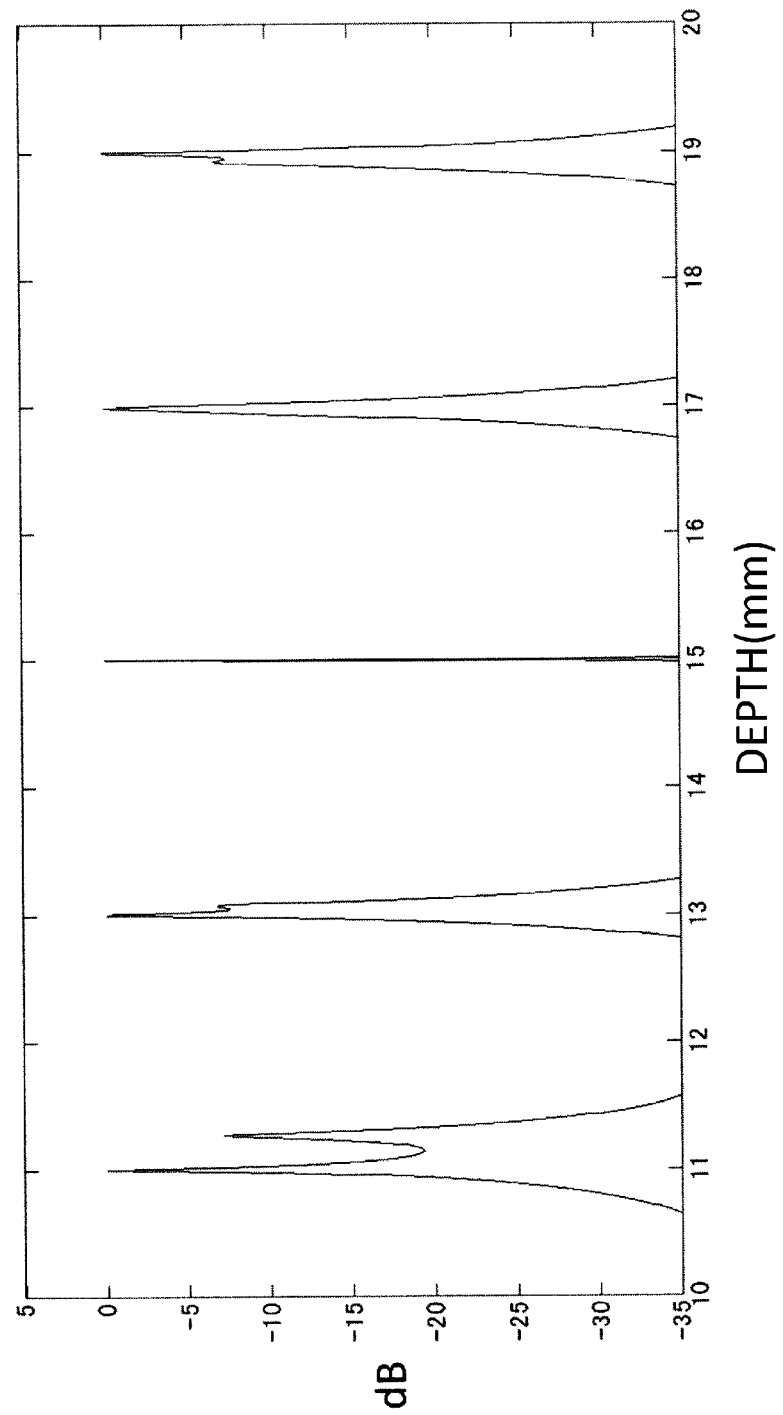
FIG. 2 is a diagram explaining the power strength when the reflected waveform shown in FIG. 1 is used as the received signal.

FIG. 2 shows the results upon performing adaptive signal processing to which the FDI method was applied by using the respective waveforms shown in FIG. 1 as the received signal, and using the transmission waveform (that is, waveform that is substantially the same as the waveform at the depth of 15 mm) as the reference signal. Note that the transmission waveform at the respective depths of FIG. 1 can be considered as being basically the same as the reflected waveform at the respective depths. In other words, using each of the waveforms shown in FIG. 1 as a received signal can be considered as being basically the same as having received a reflected waveform from the reflecting surface that exists at the position of the respective depths (11 mm, 13 mm, 15 mm, 17 mm, 19 mm).

According to the results shown in FIG. 2, the effect of high resolution can be confirmed at the depth of 15 mm where the waveform of the reference signal and the received signal are equal. Nevertheless, at the position of the depth of 11 mm, the power strength as the processing result thereof shows two peaks, and, since the half width of the peaks is also broad, it can be understood that the effect of high spatial resolution could not be sufficiently obtained. Moreover, at the other depths of 13 mm, 17 mm, and 19 mm also, the effect of high spatial resolution is lower than that obtained at the depth of 15 mm. Thus, in order to deal with this problem, the ensuing embodiments are unique in that the transmission sound pressure (conversion efficiency) of the acoustic waves in the conversion elements that transmit and receive ultrasonic waves is varied.

Moreover, the acoustic waves referred to in the present invention are typically ultrasound waves, and include elastic waves referred to as sound waves or ultrasound waves. The object information acquiring apparatus of the present invention includes apparatuses that transmit acoustic waves to an object, receives the reflected waves (reflected acoustic waves) that were reflected within the object, and acquires the acoustic properties at a plurality of positions in the object as numerical values or image data. The acquired acoustic properties are information that reflects the difference in the acoustic impedance of the tissues in the object. Moreover, the scanning line referred to in the present invention is a virtual line that is formed in the advancing direction of the acoustic waves that are transmitted from the probe.

Basic Embodiment

Embodiments of the present invention are now explained with reference to the appended drawings. As a general rule, the same constituent elements are given the same reference numeral, and the explanation thereof is omitted.

(Basic Configuration of Object Information Acquiring Apparatus)

Figure 3:
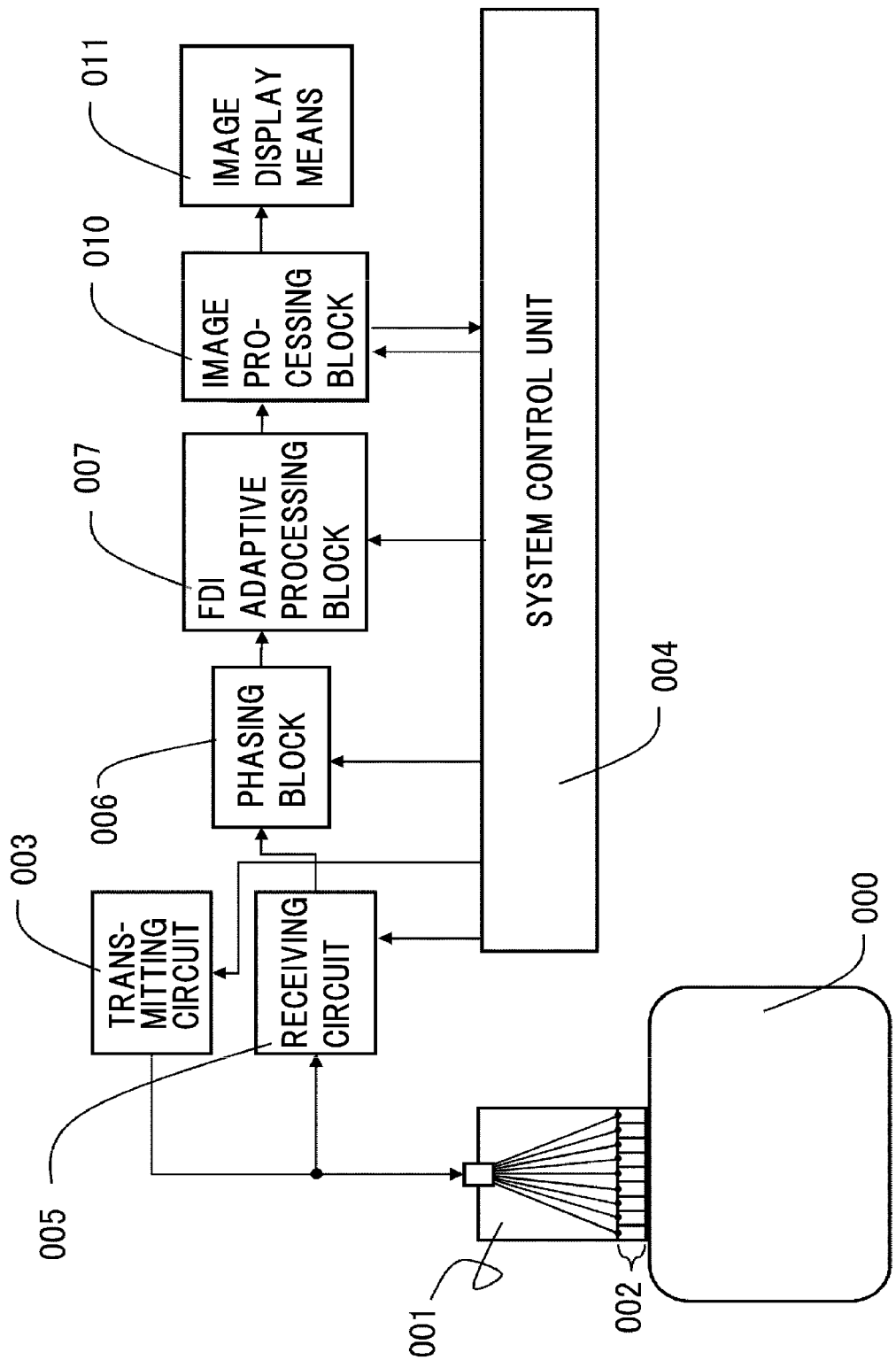
FIG. 3 is a schematic diagram showing the object information acquiring apparatus to which the present application can be applied.

FIG. 3 is a schematic diagram showing the object information acquiring apparatus to which the present application can be applied. The object information acquiring apparatus of this embodiment comprises a probe 001 including a plurality of conversion elements 002, a receiving circuit 005, a transmitting circuit 003, a phasing/addition block 006, and an FDI adaptive processing block 007. The object information acquiring apparatus additionally comprises an image processing block 010 and a system control unit 004.

In this embodiment, a processor is configured by including at least a receiving circuit 005, a transmitting circuit 003, a phasing/addition block 006, and an FDI adaptive processing block 007. The processor may additionally include a system control unit 004 and an image processing block 010.

The probe 001 is a transmitter/receiver that transmits acoustic waves to an object 000, and receives reflected waves that were reflected at a plurality of positions in the object, and comprises a plurality of conversion elements 002 that convert the acoustic waves into an electric signal (time-series received signal). As the conversion elements, used may be conversion elements such as piezoelectric elements that use the piezoelectric phenomena, conversion elements that use optical resonance, or conversion elements that use the change in capacitance such as a capacitive micromachined ultrasonic transducer (CMUT).

The transmitting circuit 003 generates a transmitted signal (pulse signal) having the delay time and amplitude according to the focusing position or focusing direction in accordance with a control signal from the system control unit 004. The transmitted signal is input to each of the plurality of conversion elements 002, and acoustic waves are transmitted from the plurality of conversion elements 002 as pulse waves to the object. The acoustic waves (reflected waves) that were reflected off the reflecting interface or reflector in the object 000 are received by the plurality of conversion elements 002, and are each converted into a plurality of received signals. The plurality of received signals that are output from the plurality of conversion elements 002 are input to the receiving circuit 005.

The receiving circuit 005 is a circuit that amplifies the received signals that were output in a time series from the respective conversion elements, and converts the received signals into a plurality of digital signals (digitized received signals), and is configured from an amplifier, an A/D converter, and the like. Note that, in the ensuing explanation, a time-series received signal that is output from one conversion element that received the reflected waves based on a single transmission of an acoustic wave pulse will be treated as one received signal. Let it be assumed that, when there are M-number of output channels, M-number of received signals corresponding to the number of output channels are obtained based on a single transmission of an acoustic wave pulse. Moreover, upon focusing on a certain conversion element, when an acoustic wave pulse is transmitted N-number of times, received signals for N-number of transmissions (that is, N-number of time-series received signals) will be obtained for that conversion element. N and M represent positive integers. Moreover, in the present invention, in addition to the analog received signals that are output from the conversion elements 002, signals that were subject to the processing of amplification and digital conversion are also represented as received signals. The plurality of digital signals that were output from the receiving circuit 005 are input to the phasing/addition block 006.

The phasing/addition block 006 performs delay processing (phasing processing) to the plurality of digital signals according to the direction or position to which the acoustic waves were transmitted, and additionally performs addition processing thereto. In other words, the phasing/addition block 006 executes phasing/addition processing. The signals (scanning line signals) that were subject to the foregoing phasing/addition processing are input to the FDI adaptive processing block 007. The scanning line signals represent the signals on the advancing direction (on the acoustic wave beam) of the acoustic waves that were subject to transmit beam forming, and the intensities (intensity signals) of the reflected waves from a plurality of positions existing on a single scanning line signal are arranged in a time series on that scanning line. A B-mode image that is displayed on a standard ultrasonic apparatus is a result of arranging the envelopes of the scanning line signal in a quantity corresponding to the number of the plurality of scanning lines.

The FDI adaptive processing block 007 performs adaptive signal processing to which FDI processing is applied (hereinafter referred to as the "FDI adaptive processing") by using a plurality of scanning line signals output from the phasing/addition block 006, and a reference signal output from the system control unit 004.

The adaptive signal processing corresponds to adaptive beam forming. In other words, the adaptive signal processing represents the processing which adaptively changes the processing parameters such as the phase and weight according to the received signal, selectively extracts the received signal of the intended wave that arrives from the targeted focusing direction or focusing position, and suppresses the received signal of other unwanted waves. In particular, the Capon method as one type of adaptive signal processing is a method of processing a plurality of input signals so that the output (power strength) is minimized in a state where the sensitivity related to the focusing direction or focusing position is fixed. This method is also known as the directionally constrained minimization of power (DCMP) or the minimum variance method. This kind of adaptive signal processing yields the effect of being able to improve the spatial resolution. In this embodiment, an example that adopts the Capon method as the adaptive signal processing is explained in detail. However, other adaptive signal processing (MUSIC method or ESPRIT method) may also be used.

Frequency Domain Interferometry (the FDI method) is a method of estimating the received power at the focusing position by decomposing the received signals for each frequency, and varying the phase of the decomposed signals according to the focusing position. Note that the variation of the phase is determined in advance based on the distance from a certain reference position to the focusing position, and the product of the wave number corresponding to the frequency.

In other words, combining the adaptive signal processing to the FDI method results in the calculation of the power strength at the focusing position by using the amount of phase shift and weight calculated according to the received signals, and not by using the predetermined amount of phase shift and weight, with regard to the received signals that were decomposed into the respective frequency components. Details of the processing performed by the FDI adaptive processing block 007 will be explained later with reference to FIG. 4. In this embodiment, the power strength calculated based on the FDI adaptive processing corresponds to the acoustic properties that reflect the difference in the acoustic impedance of the tissues in the object. Moreover, the image processing block 010 in the latter stage outputs, as image data, the power strength distribution configured from a plurality of power strengths.

The image processing block 010 performs various types of image processing as needed, such as smoothing and edge enhancement to the input power strength distribution configured from a plurality of power strengths, and outputs brightness data (image data) to the image display means 011. The image display means 011 displays the input brightness data.

Note that the FDI adaptive processing block 007 is configured, for example, from a processing unit such as a CPU, a graphics processing unit (GPU), or an field programmable gate array (FPGA) chip or the like. The system control unit 004 and the image processing block 010 are similarly configured from a processing unit such as a CPU, a GPU, or an FPGA. The image display means 011 is configured from an liquid crystal display (LCD), a cathode ray tube (CRT), an organic EL display or the like. Note that the image display means 011 is provided separately from the object information acquiring apparatus of the present invention.

(Flow of FDI Adaptive Processing)

Figure 4:
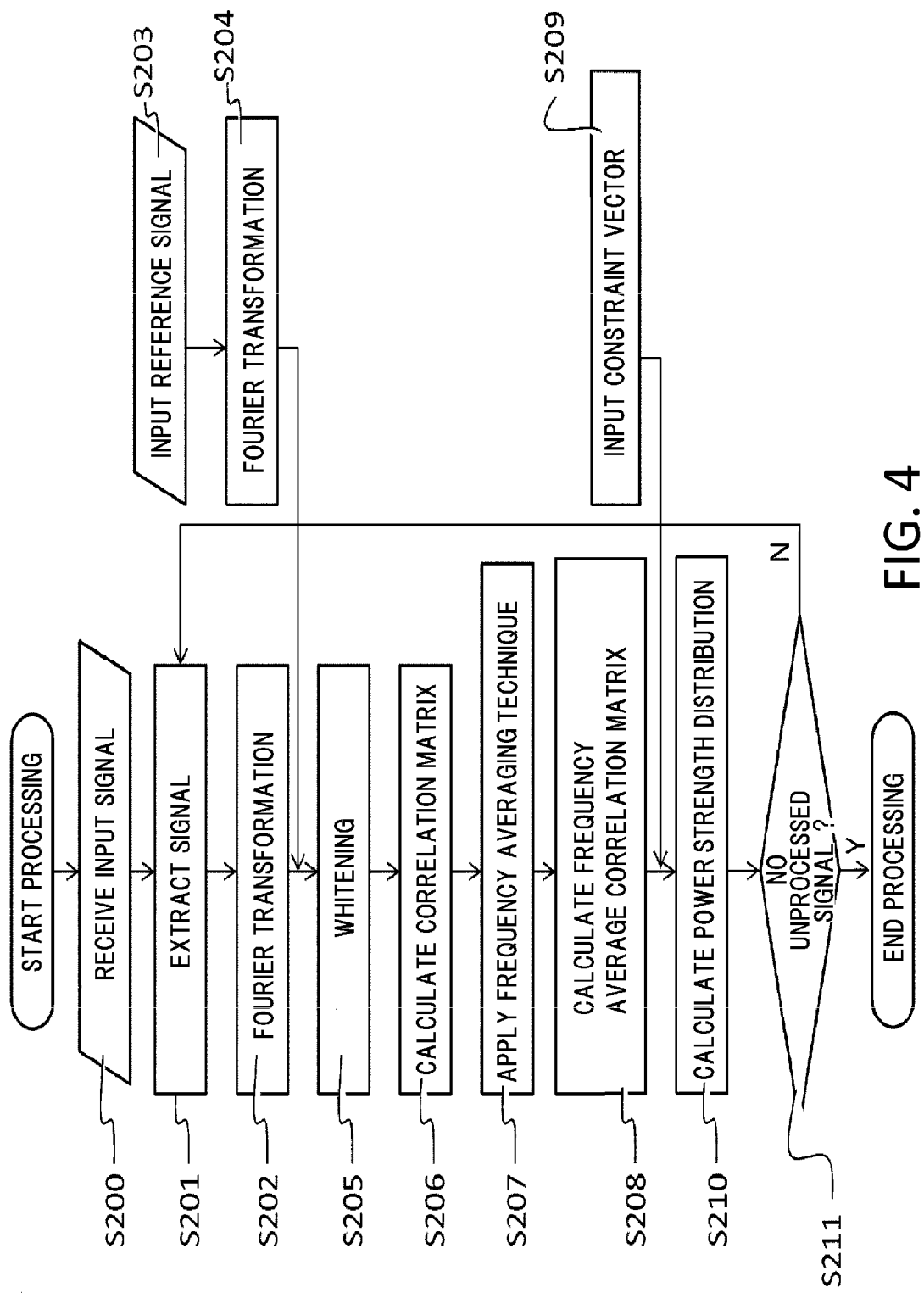
FIG. 4 is a flowchart explaining the processing that is performed by the FDI adaptive processing block.

The processing performed by the FDI adaptive processing block 007 is now explained with reference to FIG. 4. FIG. 4 is a flowchart explaining the respective steps of the FDI adaptive processing. The FDI adaptive processing block 007 receives, as input signals, the scanning line signals output from the phasing/addition block 006 (S200). The FDI adaptive processing block 007 subsequently extracts the intensity signals from the scanning line signals corresponding to the processing time of one process; that is, the intensity signals corresponding to the processing range (S201). Here, as the processing that is performed by the FDI adaptive processing block 007, in addition to extracting the signals corresponding to the processing range from the plurality of intensity signals on one scanning line, processing such as the weighting of the respective intensity signals may also be performed.

Subsequently, the extracted signal is subject to Fourier transformation and divided into components of each frequency ($Xs1, Xs2, Xs3, \ldots, XsN$) (S202). Meanwhile, the reference signal output from the system control unit 004 is input to the FDI adaptive processing block 007 (S203).

Subsequently, the FDI adaptive processing block 007 performs Fourier transformation of the reference signal, and divides the reference signal into components of each frequency ($Xr1, Xr2, Xr3, \ldots, XrN$) (S204).

Subsequently, the FDI adaptive processing block 007 performs whitening processing as shown in Formula (1) (S205).

[Math. 1]

$$X_{wk} = \frac{X_{sk} X_{rk}^*}{|X_{rk}|^2 + \eta} \quad (1)$$

Here, Xwk (k=1, 2, . . . , N) are components of each frequency after the whitening processing, η is a trace amount for stabilization, and * represents a complex conjugate.

Next, a vector X (Formula (2)) configured from the respective frequency components that were subject to whitening processing is used to calculate the correlation matrix Ras shown in Formula (3) (S206).

$$X = [X_{W1}, X_{W2}, \ldots, X_{WN}]^T \quad (2)$$

$$R = XX^{T*} \quad (3)$$

Note that T represents a transposition. Here, the correlation matrix R will be a matrix having a size of N×N.

Subsequently, a partial matrix is extracted from the correlation matrix R, and the frequency averaging technique of averaging the frequencies is applied (S207).

[Math. 2]

$$R' = \frac{1}{M}\sum_{m=1}^{M} R_m \quad (4)$$

$$R_{mij} = X_{W(i+m-1)} X_{W(j+m-1)}^* \quad (5)$$

R' is the frequency average correlation matrix, and Rm is the partial matrix of the correlation matrix R having Rmij as the member. The frequency average correlation matrix R' is thereby calculated according to Formula (4) and Formula (5) (S208).

Subsequently, a constraint vector C is input to the FDI adaptive processing block 007 (S209). The constraint vector C is a vector that changes according to the position r in the processing range, and is defined with following Formula (6).

$$C = [\exp(jk_1 r), \exp(jk_2 r), \ldots, \exp(jk_{(N-M+1)} r)] \quad (6)$$

The frequency average correlation matrix R' and the constraint vector C are used to calculate the power strength distribution P(r) in the processing range as shown in Formula (7) (S210).

[Math. 3]

$$P(r) = \frac{1}{C^{T*}(R' + \eta' E)^{-1} C} \quad (7)$$

η'E has been added to stabilize the calculation of the inverse matrix, and η is a value that changes according to the constant or the $R_{xx,1}$ value, and E is an identity matrix.

Subsequently, when there is an unprocessed signal among the input signals, the routine returns to the extraction of signals (S201), and the processing is continued (S211). When all signals have been processed, this processing is ended.

As described above, the FDI adaptive processing block 007 performs the adaptive signal processing to which the FDI method is applied by using, as the input signals, the plurality of scanning line signals output from the phasing/addition block 006, and the reference signal output from the system control unit 004. The power strength distribution is consequently output.

The conversion elements 002 are now explained. FIG. 5A is a diagram schematically showing the conversion elements of the present invention. A plurality of conversion elements are arranged in an array direction (horizontal direction in the diagram). FIG. 5B to FIG. 5D show the transmission sound pressure in a direction (vertical direction in the diagrams) that intersects with the array direction of one conversion element. The three diagrams of FIG. 5B to FIG. 5D repsectively represent the transmission sound pressure distribution of the X-X' cross section of FIG. 5A in different cases. Note that, in the ensuing explanation, the array direction of the conversion elements is sometimes referred to as a "first direction", and the direction that intersects the array direction of the conversion elements is sometimes referred to as a "second direction".

The transmission sound pressure distribution 501 of FIG. 5B has a uniform transmission sound pressure intensity up to the end portions in the direction (second direction) that intersects the array direction (first direction) of the conversion elements. The transmission sound pressure distribution 502 of FIG. 5C is a transmission sound pressure intensity in which the transmission sound pressure of the acoustic waves are lower at the end portions in the second direction than the midportion in the second direction. With the transmission sound pressure distribution 503 of FIG. 5D, the transmission sound pressure at the end portions in the second direction are even more lower than the transmission sound pressure at the midportion in comparison to the case of FIG. 5C. Note that, as shown in FIG. 5E, since the transmit beam forming of the acoustic waves is performed in the second direction, an acoustic lens 504 is provided on the object side (side to which the acoustic waves are to be transmitted) of the onversion elements 002 of the probe.

Figure 6A:
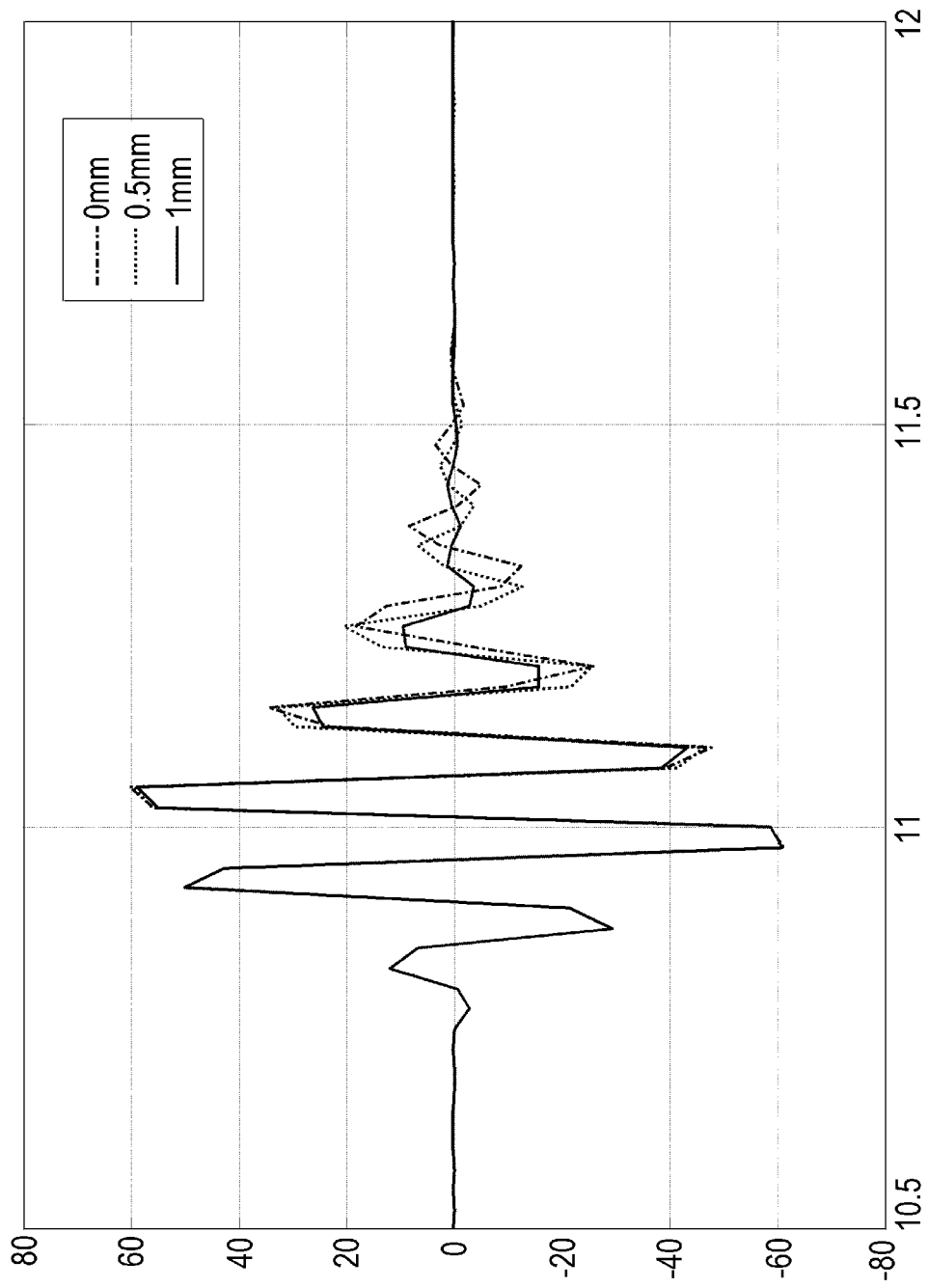
FIG. 6A is a diagram explaining the effect of the first embodiment.
Figure 6B:
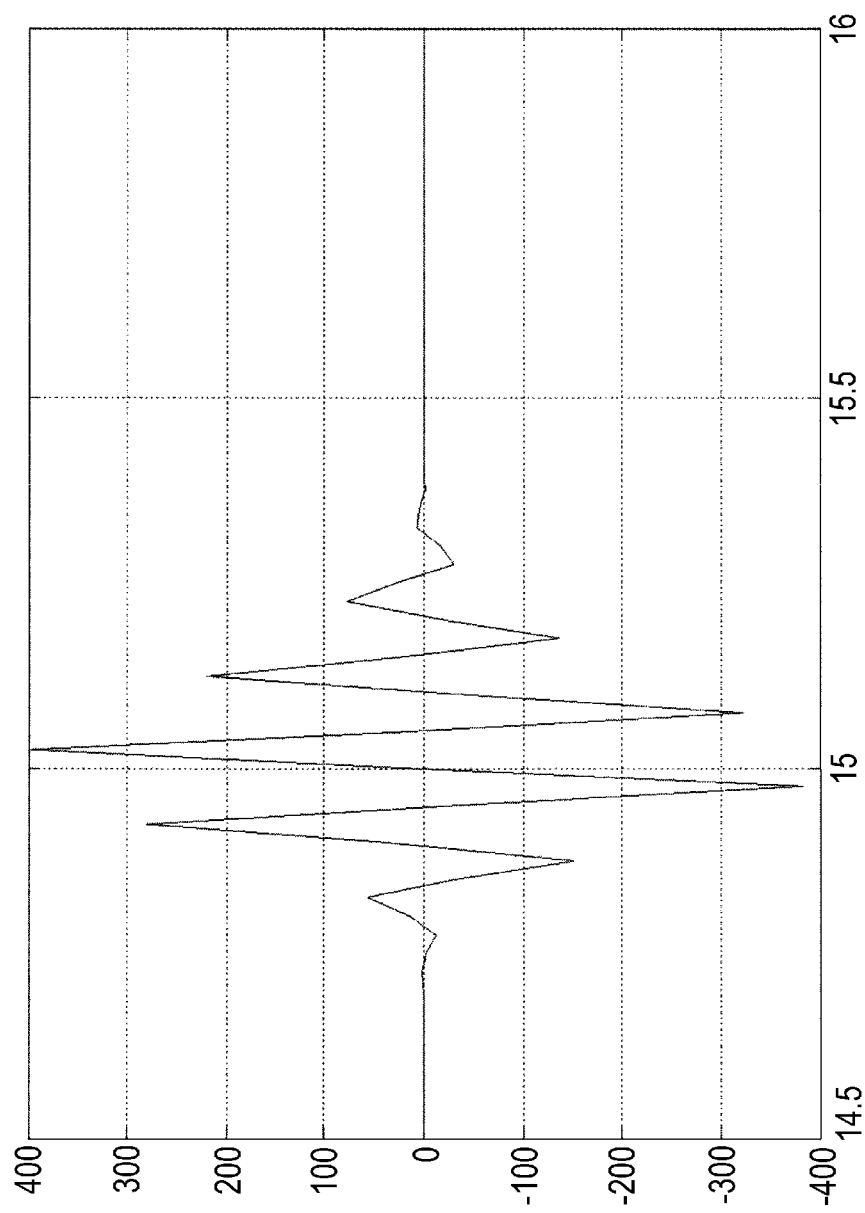
FIG. 6B is a diagram explaining the effect of the first embodiment.

FIG. 6A shows the waveform at 11 mm when the acoustic waves are transmitted to be focused at a depth of 15 mm by using the three types of transmission sound pressure distribution shown in FIG. 5B to FIG. 5D. In the diagram, the dashed line shows the waveform (corresponds to the transmission sound pressure distribution 501) when the acoustic waves are transmitted at a uniform transmission intensity distribution in a direction (second direction) that intersects with an array direction (first direction) of conversion elements having a width of 8 mm. In the diagram, the dotted line shows the waveform (corresponds to the transmission sound pressure distribution 502) when the transmission intensity distribution of 0.5 mm of the end portions in the second direction was reduced. In the diagram, the solid line shows the waveform (corresponds to the transmission sound pressure distribution 503) when the transmission intensity distribution of 1 mm of the end portions in the second direction was reduced. Moreover, FIG. 6B shows the wavelength when the acoustic waves are focused at a depth of 15 mm.

As evident from these results, by causing the end portions in the second direction to have a lower transmission sound pressure than the midportion, the transmission waveform approaches the wavelength of the depth at which it is focused. In other words, it is possible to inhibit the variation in the waveform caused by the depth.

Figure 7:
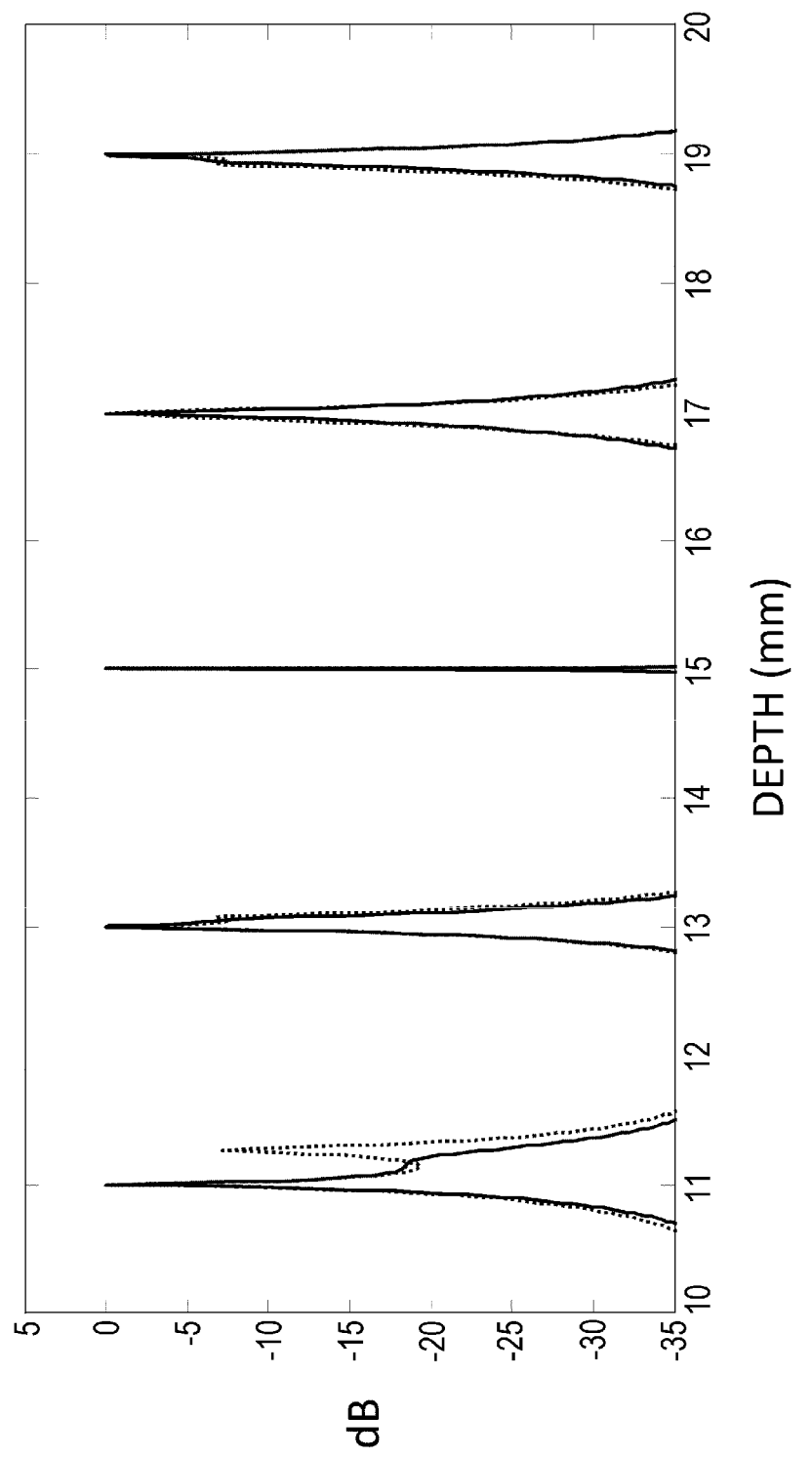
FIG. 7 is a diagram explaining the effect of the first embodiment.

FIG. 7 shows the results of performing the FDI adaptive processing by using a reference signal that gives consideration to the waveform variation at the depth of 15 mm. In the diagram, the solid line shows the processing result when the transmission sound pressure of 1 mm of the end portions of the elements of the present invention was lowered. In the diagram, the dotted line shows the processing result when the transmission sound pressure of the conversion elements are uniform. As shown with the solid line, by lowering the transmission sound pressure of the end portions of the elements, waveform variation at the respective depths can be inhibited, and it can be seen that the effect of improved spatial resolution based on the FDI adaptive processing is being stably obtained (especially at the depth of 11 mm).

Figure 8:
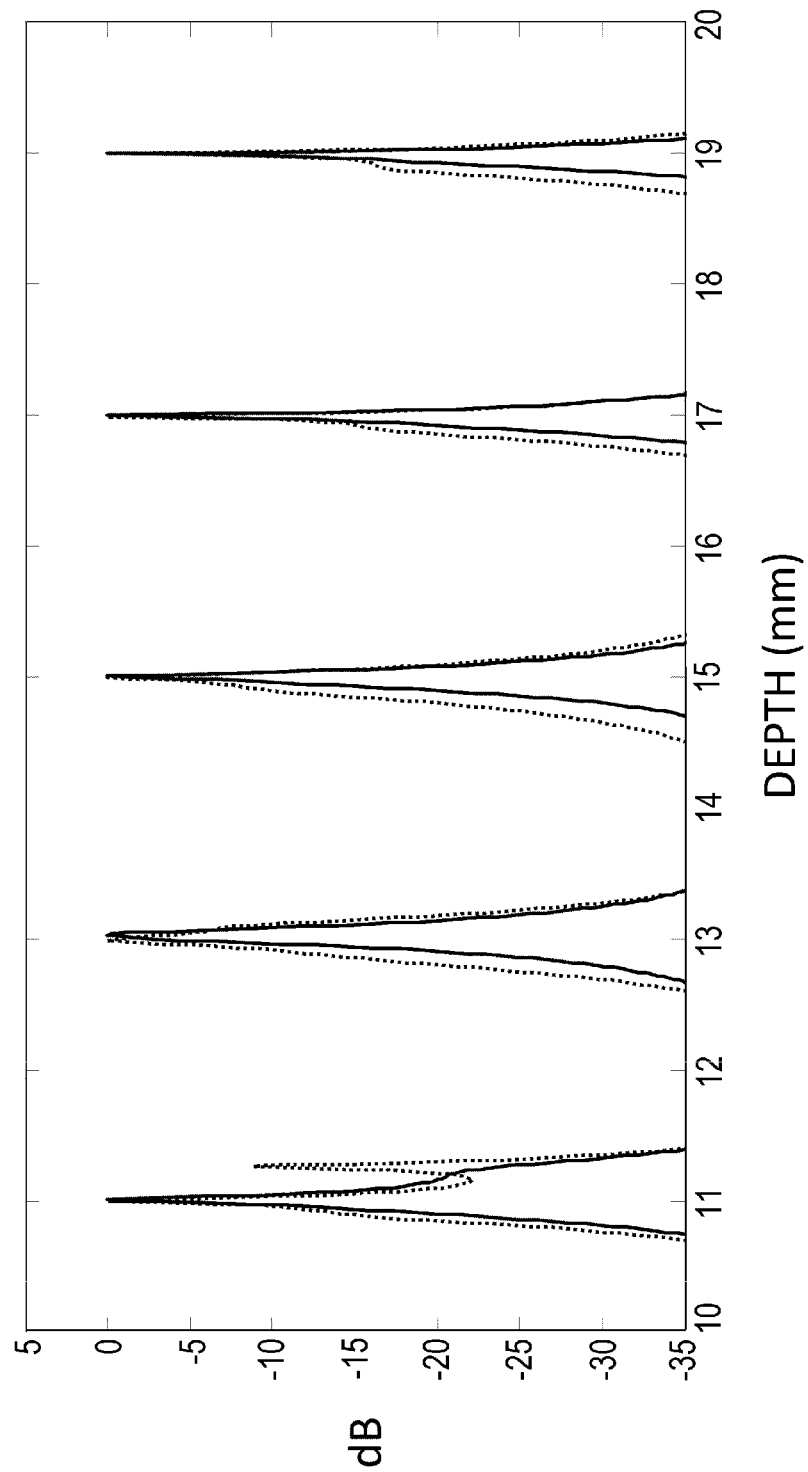
FIG. 8 is a diagram explaining the effect of the first embodiment.

FIG. 8 shows the results of performing the FDI adaptive processing by using a reference signal that gives consideration to the waveform vairation at the depth of 18 mm. In the diagram, the solid line shows the processing result when the transmission sound pressure of 1 mm of the end portions of the elements of the present invention was lowered. In the diagram, the dotted line shows the processing result when the transmission sound pressure of the conversion elements are uniform. As shown with the solid line, by lowering the transmission sound pressure of the end portions of the elements, waveform variation at the respective depths can be inhibited, and it can be seen that the effect of improved spatial resolution based on the FDI adaptive processing is being stably obtained.

As described above, by lowering the transmission sound pressure of the end portions to be lower than the transmission sound pressure of the midportion in a second direction that intersects a first direction in which the conversion elements are arranged, it is possible to yield the effects of inhibiting waveform variation for each depth, and improve the spatial resolution based on the FDI adaptive processing.

An embodiment of the object information acquiring apparatus is now explained in detail with reference to the appended drawings. Note that, as a general rule, the same constituent elements are given the same reference numeral and the explanation thereof is omitted.

First Embodiment

The object information acquiring apparatus of this embodiment adopts the same configuration as the apparatus shown in FIG. 1. In this embodiment, the shape of the conversion element 002 is described in further detail, and the explanation of the remaining processing flow is omitted since it is the same as the processing that was explained with reference to FIG. 4.

Figure 9A:
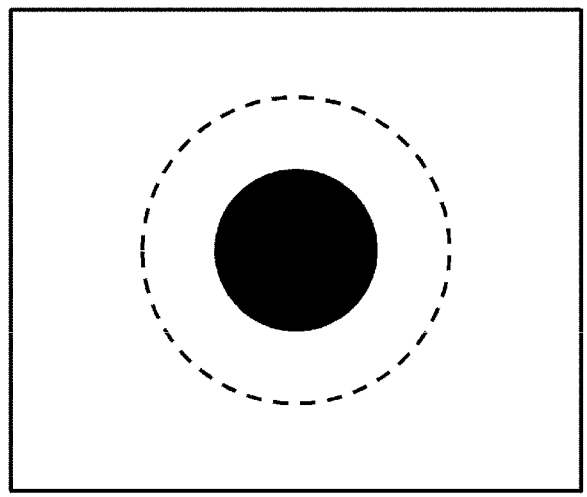
FIG. 9A and FIG. 9B are schematic diagrams explaining the structure of the CMUT.
Figure 9B:
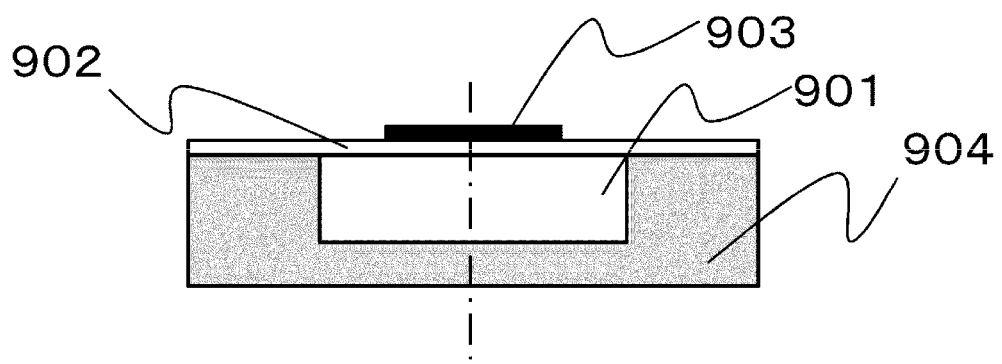

In this embodiment, a CMUT that utilizes the variance in the capacitance is used as the conversion element. FIG. 9 is a diagram schematically showing one cell in the CMUT, wherein FIG. 9A is a plan view and FIG. 9B is a cross section. In one cell, a membrane structure 902 is formed on a gap 901, and an electrode 903 is additionally placed thereon. Note that, since FIG. 9 is illustrating one cell, the illustration of the wiring connecting the electrodes 903 of the plurality of cells is omitted. In FIG. 9, a substrate 904 such as a silicon substrate is used as the counter electrode of the electrode 903. Note that it is also possible to adopt a configuration where a lower electrode is provided separately from the substrate 904.

The cell of the CMUT has a structure in which a vibrating membrane including one electrode (electrode 903 in the case of FIG. 9) of the pair of electrodes provided across from each other with a cavity (gap 901) as a gap therebetween is vibratably supported. Specifically, the vibrating membrane of FIG. 9 comprises an electrode 903 and a membrane structure 902. By inputting a voltage waveform signal (alternating voltage) to either the substrate 904 as the lower electrode or the electrode 903 as the upper electrode, the membrane structure 902 is attracted toward the gap 901 due to electrostatic attraction. Moreover, acoustic waves can be generated based on the restoration of such attraction.

Figure 10:
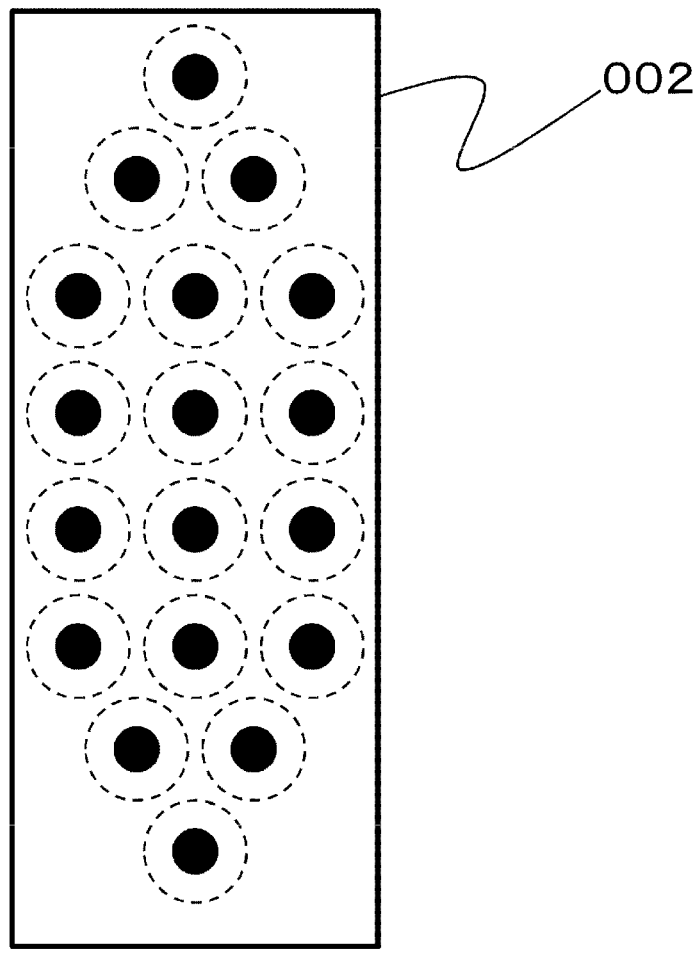
FIG. 10 is a diagram explaining the configuration of the conversion element of the first embodiment.

FIG. 10 is a schematic diagram showing one conversion element 002 (one element) of the CMUT. A plurality of cells, similar to the one shown in FIG. 9, are arranged in one element. Moreover, the conversion element array shown in FIG. 5 is formed by arranging a plurality of the elements shown in FIG. 10. The CMUT inputs and outputs signals in units of this element. In other words, when one cell is deemed as one capacity, the capacities of the plurality of cells in the element are electrically connected in parallel. Moreover, the elements are electrically isolated.

In FIG. 10, the horizontal direction is the array direction (first direction) of the conversion elements 002. In this embodiment, the number of CMUT cells (existing density) per unit area on the conversion element is reduced toward the end portions in the direction (second direction) that intersects the first direction. It is thereby possible to cause the end portions in the second direction to have a lower transmission sound pressure of acoustic waves in comparison to the midportion. Note that the effect of the present invention can be yielded by inputting the same voltage drive waveform to the CMUT cells arranged on the same conversion element 002.

As a result of transmitting acoustic waves by using the conversion elements 002 configured as described above, it is possible to inhibit the variation in the transmission waveform for each depth, and thereby more stably obtain the effect of the FDI adaptive processing.

Figure 11C:
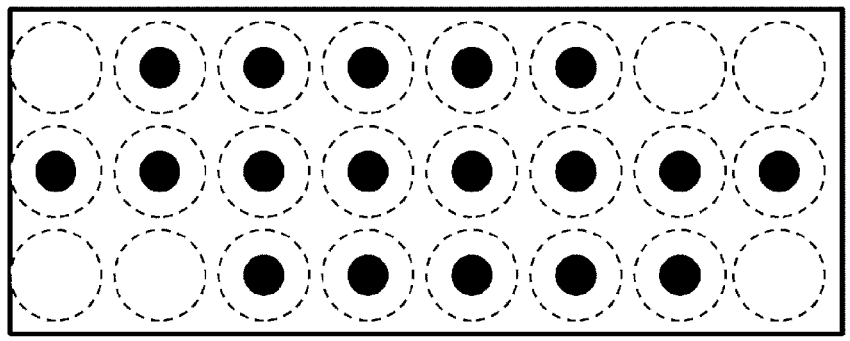
FIG. 11A to FIG. 11C are diagrams explaining the configuration of the conversion element of the first embodiment.
Figure 11B:
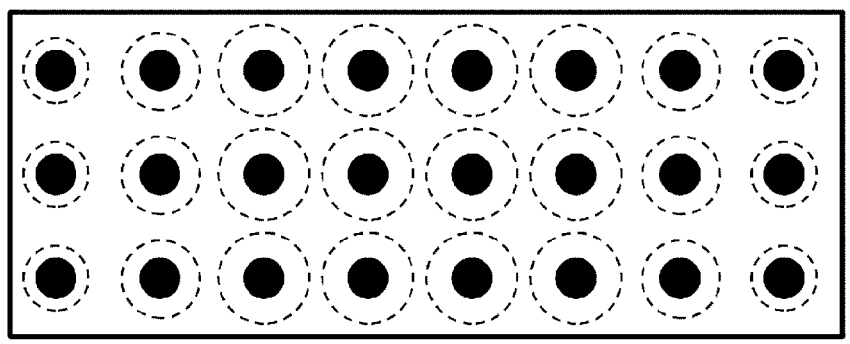
Figure 11A:
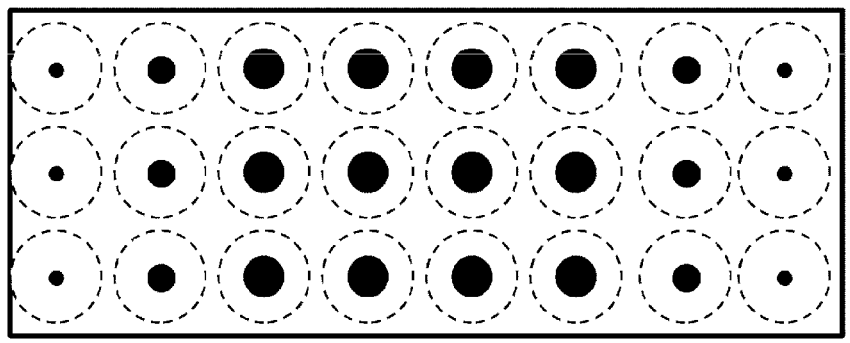

Note that, in FIG. 10, the effect of the present invention was obtained by varying the existing density of the CMUT cells. Nevertheless, the cell configuration is not limited thereto. As shown in FIG. 11A, it is also possible to adopt a configuration where the electrode size is reduced toward the end portions. Moreover, as shown in FIG. 11B, the size of the membrane structure may also be varied. Moreover, as shown in FIG. 11C, the number of cells in which an electrode is not formed may be increased toward the end portions in the membrane structure. Moreover, while not shown, the thickness of the gap may be increased toward the end portions. The effect of the present invention can be obtained with any of these methods.

Second Embodiment

The object information acquiring apparatus of this embodiment adopts the same configuration as the apparatus shown in FIG. 1. In this embodiment, a case where piezoelectric elements are used as the conversion elements 002 and arranged in a line is explained, and the explanation of the remaining processing flow is omitted since it is the same as the processing that was explained with reference to FIG. 4.

In this embodiment, a piezoelectric element such as a PZT is used as the conversion element. Specifically, as described in Patent Literature 1 (Japanese Patent Application Publication No. H6-125894), the acoustic impedance of the backing material may be changed so that the transmission sound pressure at the end portions in the second direction (direction that intersects with the first direction in which the piezoelectric elements are arranged) will be lower than the transmission sound pressure at the midportion. In other words, in the second direction, the acoustic impedance of the backing material positioned on the rear face of the midportion of the piezoelectric element is caused to be closer to the acoustic impedance of the piezoelectric element than the acoustic impedance of the backing material positioned on the rear face of the end portions.

Moreover, as described in Patent Literature 2 (Japanese Examined Patent Publication No. H1-24479) and Patent Literature 3 (Japanese Examined Patent Publication No. H1-24480), the piezoelectric element itself may be processed so that the transmission sound pressure at the end portions in the second direction will be lower than the transmission sound pressure at the midportion.

Accordingly, by transmitting acoustic waves from a probe using the piezoelectric elements configured according to this embodiment, it is possible to inhibit the variation in the transmission waveform for each depth, and thereby more stably obtain the effect of the FDI adaptive processing.

Third Embodiment

The object information acquiring apparatus of this embodiment adopts the same configuration as the apparatus shown in FIG. 1. This embodiment explains a case where the plurality of conversion elements 002 are arranged two-dimensionally in the manner of a 1.5D array, a 1.75D array, or a 2D array. The explanation of the remaining processing flow is omitted since it is the same as the processing that was explained with reference to FIG. 4.

Figure 12:
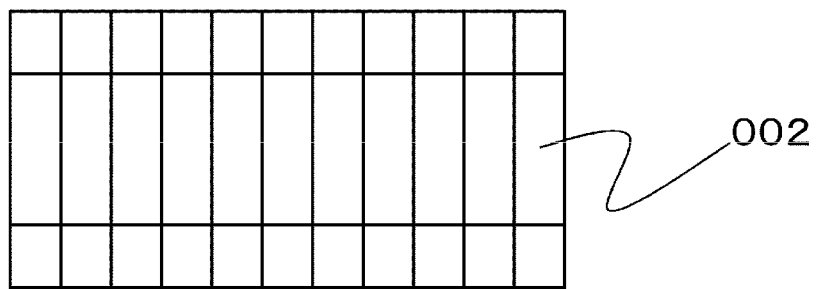
FIG. 12 is a diagram explaining the configuration of the conversion element of the third embodiment.

In this embodiment also, a CMUT, a piezoelectric element or any other kind of conversion element may be used. Moreover, even in the example of arranging the conversion elements two-dimensionally, the sound pressure at the end portions in the second direction (direction that intersects with the first direction as the array direction of the conversion elements) can be lowered by devising the configuration of the CMUT, the piezoelectric element or the backing material as with the first and second embodiments. However, in this embodiment, it is not always necessary to devise the configuration of the CMUT or devise the configuration of the piezoelectric element or the backing material in order to lower the sound pressure at the end portions in the second direction. In other words, by devising the transmitted signal for transmitting the acoustic waves, the effect of the present invention can also be obtained with a conversion element having a uniform structure in the second direction. In the ensuing explanation, particularly as shown in FIG. 12, a case of devising the transmitted signal in a 1.5D array is explained. Here, in the case of using a 1.5D array, the array direction of the conversions shows the direction of performing the electron scanning (horizontal direction in FIG. 12). In other words, this is the electron scanning direction (that is, linear scanning direction) in cases of sequentially switching the combination of the conversion element group to perform the transmit beam forming of the acoustic waves, and performing the electron scanning from one end to the other end of the conversion element group.

In this embodiment, the amplitude (intensity) of the transmitted signal to be input to the conversion elements at the end portions in the second direction (vertical direction in FIG. 12) in the probe is caused to be smaller than the amplitude (intensity) of the transmitted signal to be input to the conversion elements at the midportion. It is thereby possible to cause the conversion elements at the end portions in the second direction to have a smaller transmission sound pressure than the conversion elements at the midportion. Moreover, in this embodiment, delay time is provided between the transmitted signals to be input to the plurality of conversion elements 002 arranged in the second direction. In other words, by additionally providing a time difference to the transmitted signals to the conversion elements 002 in the direction that intersects with the electron scanning direction, the acoustic waves can also be focused in the second direction without having to provide a lens. Specifically, the transmitted signals to be input to the conversion elements at the midportion should be delayed relative to the transmitted signals to be input to the conversion elements at the end portions in the intersecting direction. Needless to day, in this embodiment also, acoustic waves can be focused in the second direction by providing a lens on the front face side of the conversion elements.

Consequently, the probe of this embodiment can also be configured so that the transmission sound pressure will be lower at the end portions in the second direction than the midportion in the second direction. Hence, it is possible to inhibit the variation in the transmission waveform for each depth, and thereby more stably obtain the effect of the FDI adaptive processing. Moreover, in the case of a 2D array, there are cases where sector scanning is performed using all conversion elements of the 2D array. With this kind of 2D array, in addition to lowering the transmission sound pressure of the conversion elements at the end portions in the second direction, the transmission sound pressure of the conversion elements at the end portions in the first direction may also be lowered. In other words, rather than just lowering the transmission sound pressure of the conversion elements at the end portions in one direction, the transmission sound pressure of the conversion elements at the outer periphery of the 2D array should also be lowered than the conversion elements at the midportion.

Fourth Embodiment

Figure 13:
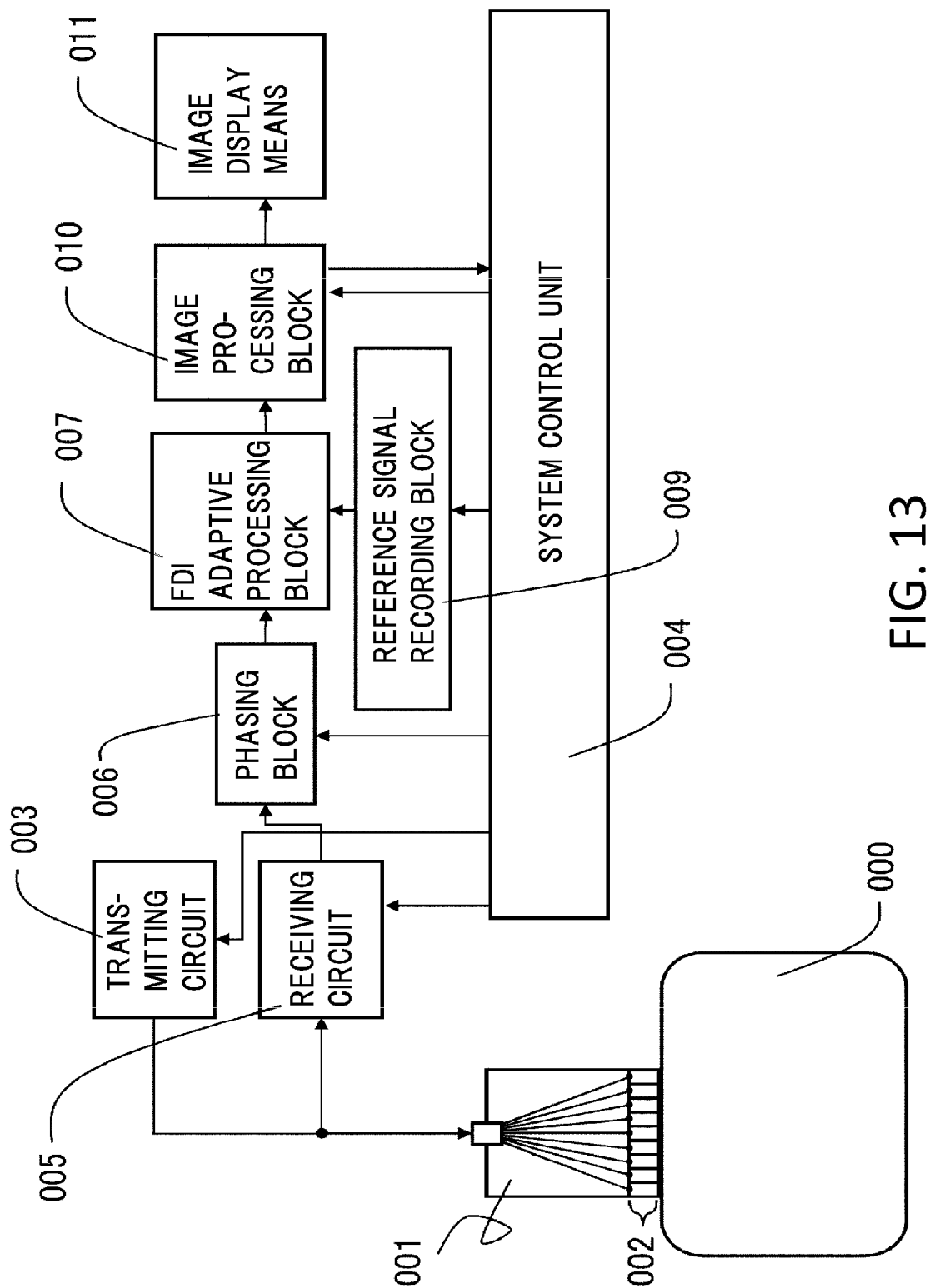
FIG. 13 is a schematic diagram showing the object information acquiring apparatus of the fourth embodiment.

FIG. 13 is a diagram schematically showing the configuration of the object information acquiring apparatus used in this embodiment. What is different from the foregoing embodiments is that a reference signal recording block 009 is provided. The reference signal recording block 009 is a memory for storing a plurality of reference signals of different waveforms in correspondence with the positions in the object. Specifically, the reference signal recording block 009 stores a plurality of reference signals each having a different waveform in correpondence with the position in the depth direction in the object, or a plurality of reference signals each having a different waveform according to the transmit direction of the acoustic waves. Moreover, the reference signal recording block 009 may also store a plurality of reference signals that change according to both the depth and the transmit direction. Upon outputting a reference signal from the reference signal recording block 009, there is no need to output all reference signals that are stored in the reference signal recording block 009.

The operation of the reference signal recording block 009 and the operation of the system control unit 004 that differ from the foregoing embodiments are specifically explained. Note that the processor in this embodiment may include the reference signal recording block 009 in addition to the processors of the foregoing embodiments.

The system control unit 004 instructs the reference signal recording block 009 to output two or more respectively different reference signals while the FDI adaptive processing block 007 is performing the FDI adaptive processing. In other words, the FDI adaptive processing block 007 performs the FDI adaptive processing by switching the reference signal at least once according to the position in the object. In particular, the reference signal is switched at least once according to either the depth (that is, reception time of the reflected waves) or the transmit direction of the acoustic waves.

In particular, in the mode of switching the reference signal according to the depth, the reference signal is switched at least once while the FDI adaptive processing is being performed using a single scanning line signal. In other words, the FDI adaptive processing is performed by using different reference signals for the intensity signal at the first position on a single scanning line signal and the intensity signal of a second position (that is different from the first position) on the same scanning line signal. However, there is no need to switch the reference signal each time for each position. When processing a single scanning line signal, the reference signal should be switched at least once according to the position; for instance, the FDI adaptive processing may be performed using the first reference signal each time in a shallow range in the object, and the FDI adaptive processing may be performed by using the second reference signal each time in a deep range. Moreover, there is no need to prepare a reference signal for each position. A reference signal may be prepared for each range of a predetermined scope. The plurality of power strengths obtained as described above are output to the image processing block 010.

When this kind of processing is performed, it is still possible to inhibit the variation in the transmission waveform for each depth based on the configuration of lowering the transmission sound pressure of the acoustic waves at the end portions in the second direction (direction that intersects with the array direction of the conversion elements) than at the midportion. In addition, in this embodiment, by using a reference signal that corresponds with the change in the transmission waveform, the effect of being able to more stably execute the FDI adaptive processing is obtained.

Figure 14:
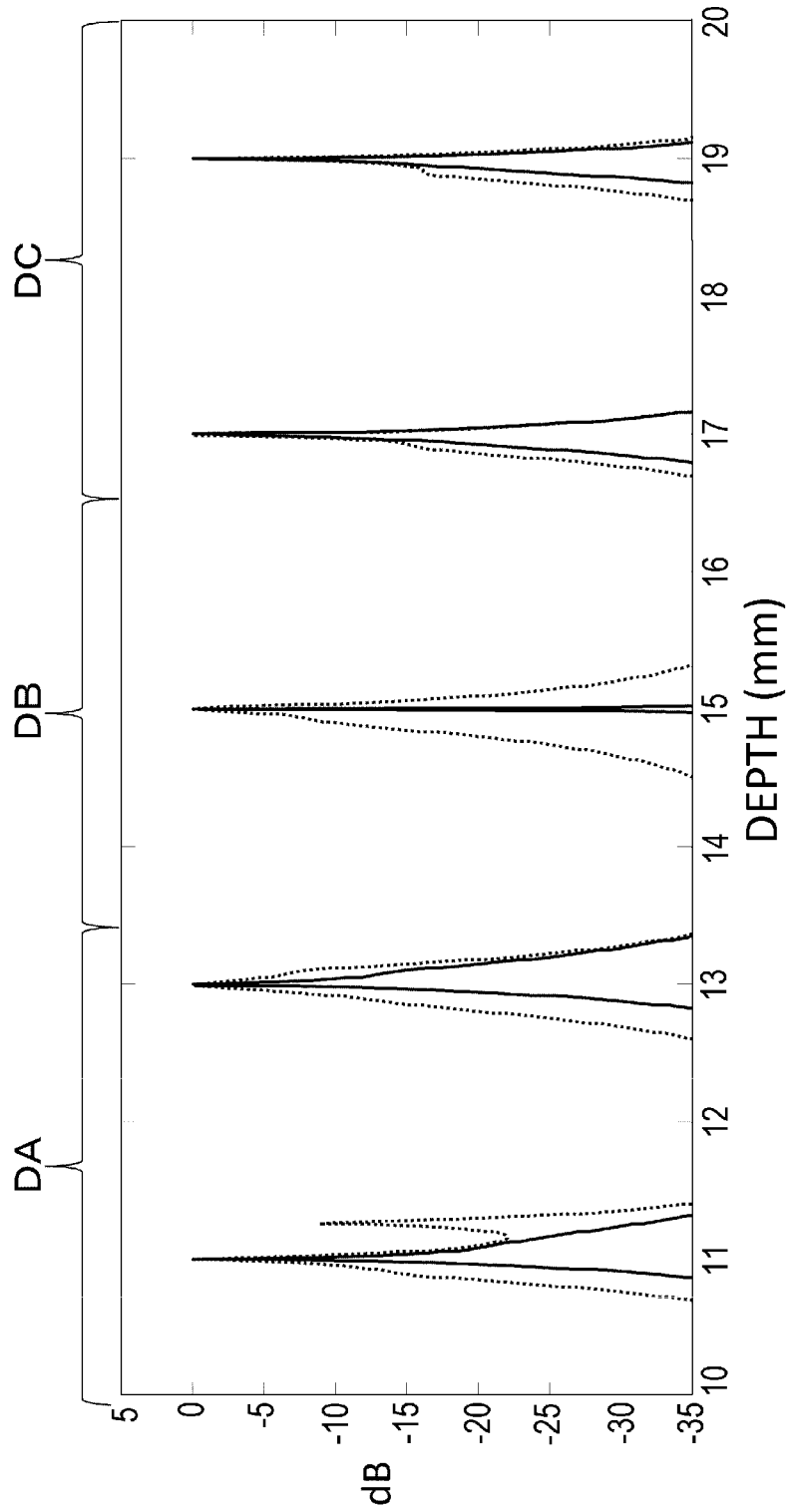
FIG. 14 is a diagram explaining the effect of the fourth embodiment.

FIG. 14 shows the result of implementing the processing according to this embodiment.

The solid line in the diagram shows the processing result in the case of using conversion elements in which transmission intensity distribution of 1 mm of the end portions was reduced. The FDI adaptive processing was performed using reference signals that gave consideration to the waveform at the depth of 12 mm in the range DA, the depth of 15 mm in the range DB, and the depth of 18 mm in the range DC. In the diagram, the dotted line shows the processing result when the transmission sound pressure of the conversion elements are uniform, and the FDI adaptive processing was performed using the waveform at the depth of 18 mm. Upon comparing the two, as shown with the solid line, by using a reference signal according to the depth rather than just lowering the transmission sound pressure of the end portions of the elements, it can be seen that the effect of being able to further improve the spatial resolution is yielded.

Fifth Embodiment

In each of the foregoing embodiments, conversion elements that function both as transmitters and receivers, which are capable of both transmitting and receiving ultrasonic waves, are used as the conversion elements 002 of the probe 001. Nevertheless, the present invention can also use separate conversion elements as a conversion element group for transmission and a conversion element group for reception. In other words, the present invention can also be realized with a configuration of connecting the conversion elements for transmission to the transmitting circuit 003, and connecting different conversion elements for reception to the receiving circuit 005. In the foregoing case, the fact that it is possible to inhibit the variation in the transmission waveform for each depth by lowering the sound pressure output at the end portions in the second direction in the conversion elements for transmission is as explained in each of the foregoing embodiments. In addition, the effect of the present invention can also be obtained with a configuration of lowering the reception intensity of the sound pressure at the end portions in the conversion elements for reception. This is based on the correlation between the transmission waveform and the reception waveform.

Sixth Embodiment

Meanwhile, with imaging methods such as Doppler and elastography, the speed and hardness are calculated by using the phase or correlation of the received signals. In this kind of processing that uses the foregoing phase or correlation, preferably the waveform of the received signal has less strain, and, for example, a waveform of a transmission focus position is desirable. The reception waveform obtained in the present invention hardly varies in the depth direction, and since the waveform of a non-focused position approaches the waveform of a focused position, imaging methods such as Doppler and elastography can be performed with greater accuracy. Accordingly, the present invention is not limited to the FDI adaptive processing, and can also be applied to imaging methods that adopt focus processing of transmitted and received signals.

Seventh Embodiment

Moreover, the present invention can also be realized by executing the following processing. In other words, the processing of supplying software (program) capable of realizing the functions of each of the foregoing embodiments to a system or an apparatus via a network or various storage mediums, and the computer (CPU, MPU or the like) of that system or apparatus reading and executing the program. The present invention can also be deemed an object information acquiring method in which the respective blocks of the object information acquiring apparatus execute the processing, or a control method of the object information acquiring apparatus.

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., non-transitory computer-readable medium). Therefore, the computer (including the device such as a CPU or MPU), the method, the program (including a program code and a program product), and the non-transitory computer-readable medium recording the program are all included within the scope of the present invention.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-092668, filed on Apr. 25, 2013, which is hereby incorporated by reference herein its entirety.

What is claimed is:

1. An object information acquiring apparatus, comprising:
a probe including a plurality of conversion elements arranged in a first direction and that transmits acoustic waves to an object, receives reflected waves that were reflected within the object, and converts the reflected waves into time-series received signals; and
a processor that performs frequency domain interferometry, through application of adaptive signal processing, by using a plurality of the received signals output from the plurality of conversion elements and a reference signal, and obtains acoustic properties of a plurality of positions in the object,
wherein the probe is configured such that end portions in a second direction intersecting the first direction have a lower transmission sound pressure of the acoustic waves than a midportion in the second direction,
wherein the reference signal is determined based on a waveform of the acoustic waves that are transmitted from the conversion elements to a predetermined depth of the object, and
wherein the processor switches the reference signal according to the depth at which the plurality of conversion elements transmit the acoustic waves to the object.

2. The object information acquiring apparatus according to claim 1, wherein the predetermined depth is a depth of a transmission focus when the plurality of conversion elements perform electronic scanning in the first direction.

3. The object information acquiring apparatus according to claim 1,
wherein the plurality of conversion elements are arranged in a line, and
wherein the probe includes an acoustic lens provided on a side of the plurality of conversion elements that transmits the acoustic wave.

4. The object information acquiring apparatus according to claim 1, wherein each of the plurality of conversion elements is configured from a CMUT including a plurality of cells.

5. The object information acquiring apparatus according to claim 4, wherein, with the CMUT, density of the cells is lower at the end portions in the second direction than the midportion in the second direction.

6. The object information acquiring apparatus according to claim 4, wherein, with the CMUT, an electrode of the cells is smaller at the end portions in the second direction than the midportion in the second direction.

7. The object information acquiring apparatus according to claim 1, wherein each of the plurality of conversion elements is configured from a piezoelectric element.

8. The object information acquiring apparatus according to claim 1,
wherein, in the probe, a plurality of conversion elements are also arranged in the second direction, and
wherein the conversion elements at the end portions in the second direction are configured to have a lower transmission sound pressure of the acoustic waves than the conversion elements at the midportion in the second direction.

9. The object information acquiring apparatus according to claim 1,
wherein, in the probe, a plurality of conversion elements are also arranged in the second direction, and
wherein transmission of the acoustic waves from the conversion elements at the end portions in the second direction is delayed relative to transmission of the acoustic waves from the conversion elements at the midportion in the second direction.

10. An object information acquiring apparatus comprising:
a probe including a plurality of conversion elements arranged in a first direction and that transmits acoustic waves to an object, receives reflected waves that were reflected within the object, and converts the reflected waves into time-series received signals; and
a processor that performs frequency domain interferometry, through application of adaptive signal processing, by using a plurality of the received signals output from the plurality of conversion elements and a reference signal, and obtains acoustic properties of a plurality of positions in the object,
wherein the probe is configured such that end portions in a second direction intersecting the first direction have a lower transmission sound pressure of the acoustic waves than a midportion in the second direction,
wherein the reference signal is determined based on a waveform of the acoustic waves that are transmitted from the conversion elements to a predetermined depth of the object, and
wherein the processor switches the reference signal according to the direction in which the plurality of conversion elements transmit the acoustic waves to the object.

11. An object information acquiring apparatus, comprising:
a probe including a conversion element group for transmission having a plurality of conversion elements that transmit acoustic waves to an object, and a conversion element group for reception having a plurality of conversion elements that receive reflected waves reflected within the object, and convert the reflected waves into time-series received signals; and
a processor configured to perform frequency domain interferometry, through application of adaptive signal processing, by using a plurality of the received signals output from the conversion element group for reception and a reference signal, and obtaining acoustic properties of a plurality of positions in the object,
wherein the probe is configured such that, when a direction in which the plurality of conversion elements of the conversion element group are arranged is a first direction and a direction which intersects with the first direction is a second direction, reception intensity of the acoustic waves is lower at the end portions in the second direction than at the midportion in the second direction in the conversion element group for reception,
wherein the reference signal is determined based on a waveform of the acoustic waves that are transmitted from the conversion elements to a predetermined depth of the object, and
wherein the processor switches the reference signal according to the depth at which the plurality of conversion elements transmit the acoustic waves to the object.

12. A control method of an object information acquiring apparatus having a probe including a plurality of conversion elements arranged in a first direction and that transmits and receives acoustic waves, and a processor, with the probe being configured so that end portions in a second direction intersecting the first direction have a lower transmission sound pressure of the acoustic waves than a midportion in the second direction, the control method comprising:
- a step of operating the plurality of conversion elements to transmit acoustic waves to an object;
- a step of operating the plurality of conversion elements to receive reflected waves reflected within the object, and convert the reflected waves into time-series received signals;
- a step of operating the processor to perform frequency domain interferometry, through application of adaptive signal processing, by using a plurality of the received signals output from the plurality of conversion elements, and a reference signal, and obtain acoustic properties of a plurality of positions in the object,
- wherein the reference signal is determined based on a waveform of the acoustic waves that are transmitted from the conversion elements to a predetermined depth of the object; and
- a step of operating the processor to switch the reference signal according to the depth at which the plurality of conversion elements transmit the acoustic waves to the object.

13. A non-transitory computer-readable storage medium storing one or more programs, the one or more programs comprising instructions, which when executed by one or more processors of a computer, cause the computer to execute the respective steps of the control method according to claim 12.

14. A control method of an object information acquiring apparatus having a probe including a conversion element group for transmission having a plurality of conversion elements that transmit acoustic waves and a conversion element group for reception having a plurality of conversion elements that receive reflected waves, and a processor, with the probe being configured such that, when a direction in which the plurality of conversion elements of the conversion element group are arranged is a first direction and a direction which intersects with the first direction is a second direction, reception intensity of the acoustic waves is lower at the end portions in the second direction than at the midportion in the second direction in the conversion element group for reception, the control method comprising:
- a step of operating the conversion element group for transmission to transmit acoustic waves to an object;
- a step of operating the conversion element group for reception to receive reflected waves reflected within the object, and convert the reflected waves into time-series received signals; and
- a step of operating the processor to perform frequency domain interferometry, through application of adaptive signal processing, by using a plurality of the received signals output from the conversion element group for reception and a reference signal, and obtain acoustic properties of a plurality of positions in the object,
- wherein the reference signal is determined based on a waveform of the acoustic waves that are transmitted from the conversion elements to a predetermined depth of the object, and
- wherein the processor switches the reference signal according to the depth at which the plurality of conversion elements transmit the acoustic waves to the object.

* * * * *